(12) United States Patent
Hietala (10) Patent No.: US 8,333,111 B2
(45) Date of Patent: Dec. 18, 2012

(54) METHOD AND ARRANGEMENT FOR DETERMINING SAMPLE FLOW VOLUME

(75) Inventor: Mika Hietala, Espoo (FI)

(73) Assignee: General Electric Company, Schenectady, NY (US)

(*) Notice: Subject to any disclaimer, the term of this patent is extended or adjusted under 35 U.S.C. 154(b) by 315 days.

(21) Appl. No.: 12/858,857

(22) Filed: Aug. 18, 2010

(65) Prior Publication Data

US 2011/0067480 A1    Mar. 24, 2011

(30) Foreign Application Priority Data

Sep. 24, 2009  (EP) .................................. 09396008

(51) Int. Cl.
*G01F 17/00* (2006.01)
*G01N 33/497* (2006.01)
*A61B 5/08* (2006.01)

(52) U.S. Cl. .................. 73/149; 73/23.3; 600/529
(58) Field of Classification Search .......... 73/23.3, 73/23.4, 149; 600/529, 532
See application file for complete search history.

(56) References Cited

U.S. PATENT DOCUMENTS

| | | | |
|---|---|---|---|
| 5,398,695 A | 3/1995 | Anderson et al. | |
| 7,335,164 B2 * | 2/2008 | Mace et al. | 600/532 |
| 2003/0208131 A1 * | 11/2003 | George | 600/532 |
| 2003/0208133 A1 * | 11/2003 | Mault | 600/532 |

FOREIGN PATENT DOCUMENTS

| | | |
|---|---|---|
| EP | 0392503 A2 | 10/1990 |
| EP | 1547523 A1 | 6/2005 |
| WO | 2000072754 A1 | 12/2000 |
| WO | 2009053958 A1 | 4/2009 |

OTHER PUBLICATIONS

Shakya, K; et al. "Dynamic Response Measurement of Clinical Gas Analysers," Computer-Based Medical Systems, 2005. Proceedings. 18th IEEE Symposium on Dublin, Ireland, Jun. 23-24, 2005, Piscataway, New Jersey, United States of America (Jun. 23, 2005), pp. 165-170, XP010818002.

(Continued)

*Primary Examiner* — John Fitzgerald
*Assistant Examiner* — David Z Huang
(74) *Attorney, Agent, or Firm* — Global Patent Operation (57) ABSTRACT

A method for determining a sample flow volume is disclosed herein. The method includes withdrawing the sample flow at a first and second flow rate from a gas flow, measuring a concentration of at least one gas component and measuring at least one of an airway pressure and flow. The method also includes generating first measurement results based on the concentration, generating second measurement results based on the at least one of the airway pressure and flow and setting a suitable point of comparison. The method further includes determining a first and second time delay between the point of comparison of the first and second measurement results of the first and second flow rate, providing information about the first and second sample flow rate and determining the sample volume based on differences between the first and second time delay. A corresponding arrangement is also provided.

20 Claims, 3 Drawing Sheets

OTHER PUBLICATIONS

Franck Verschuren, Erkki Heinonen, Didier Clause, Francis Zech, Marc Reynaert, Giuseppe Liistro. "Volumetric capnography: reliability and reproducibility in spontaneously breathing patients." Clinical Physiology and Functional Imaging, Sep. 30, 2005, pp. 275-280, XP002566175, Philadelphia, Pennsylvania, United States of America.

Breen, P.H. and Serina E.R. "Bymixer provides on-line calibration of measurement of $CO_2$ volume exhaled per breath," Annuls of Biomedical Engineering, vol. 25, Jan. 1, 1997, pp. 164-171, XP002566176, United States of America.

EP Search Report for EP Application 09396008 filed on Sep. 24, 2009 issued on Feb. 16, 2010.

* cited by examiner

METHOD AND ARRANGEMENT FOR DETERMINING SAMPLE FLOW VOLUME

BACKGROUND OF THE INVENTION

1. Field of Invention

This disclosure relates generally to a method and arrangement for determining a sample flow volume.

2. Description of the Prior Art

Breath gases are measured in hospitals for several reasons and several departments. Typical measured gases are one or several of the following gases: CO2, O2, N2O and anesthetic gases (halothane, sevoflurane, desflurane, isoflurane and enflurane). CO2 measurement can also be used to determine respiration rate. Gases are measured either using a sidestream (non-diverting) technique or a mainstream (diverting) technique. The sidestream technique means that the gas sample is transferred along a sampling line from a gas channel, which is between a patient and a ventilator, to a sensor, which causes a delay between breath and measurement. Mainstream technique means that sample is analyzed at sampling site, which is typically in the gas channel between the patient and the ventilator.

Spirometry measurement is used to measure lung function by measuring the flow and pressure of the inhaled and exhaled air. The volume of the breath can be calculated of those parameters.

By combining the breath gas measurement and the spirometry measurement a gas exchange measurement can be performed. It means that by synchronizing gas measurement concentration curves of carbon dioxide (CO2) and oxygen (O2) and spirometry flows and pressures, the oxygen consumption (VO2) and produced carbon dioxide (VCO2) can be measured. These parameters reflect the metabolic component of body systems and can be used to further calculate a respiratory quotient (RQ) and an energy expenditure (EE). The continuous and non-invasive measurement of respiratory gas exchange, also known as indirect calorimetry, is potentially valuable when employed for diagnostic and therapeutic purposes.

The sidestream measurement includes a delay, which can be from one to several seconds depending on the sampling line length, sample line inner diameter and sample flow rate. The spirometry measurement does not include this delay and therefore the right synchronization of these measurements is crucial for the gas exchange measurement. There is no good and reliable method to identify which spirometry breath cycle belongs to which gas measurement cycle. This problem in synchronization is the bigger the higher is the respiration rate. The delay between these measurements may be even a few breathing cycles long.

The synchronization would be quite easy if there was only one sample line length and only one sample line inner diameter available because then the sampling volume, which is the volume between the end of sampling line, which is a point of contact where the sampling line is connected to the gas channel, and gas sensor, would be known. The synchronization is performed by integrating the sampling flow rate acquired by the internal flow sensor in the gas measuring unit starting for example from a beginning of an inspiration and integrating as long as the sampling line volume is reached and selecting the nearest beginning of the inspiration from the gas sensor. If there is one beginning of the inspiration much nearer than the second nearest, then the synchronization was successful. Usually there are, however, many lengths of sampling lines and even many sample line inner diameters available and therefore that technique can't be used or it is unreliable.

The synchronization can be performed also utilizing the previous technique if there are for example two sample line lengths and one sample line inner diameter or one sample line length and two sample line inner diameters available but then the successfulness of the synchronization depends on whether breathing rate is suitable. At high breathing rates this technique usually can't be used because the time between beginning of breathing cycles is short and uncertainty, which breathing cycle is the right one, is too big.

The sampling line volume and sampling delay can be determined also by stopping a pump withdrawing the gas from the gas channel to the sidestream gas sensor and waiting for some breathing cycles. There will be mixed air in the end of the sampling line which is close to the gas channel. By starting the pump and calculating the time and sampling line volume till the mixed air receives the gas sensor, the sample volume and delay time can be determined and the synchronization usually is successful. The problem is that this technique forces to stop the pump so the gas measurement is not available for many seconds.

A present well-known theoretical background of a technique for synchronization is based on an adjustment of the sample flow rate. The sampling volume Vsample is an integral of the sample flow rate integrated for delay time, Tdelay:

$$Vsample = \int_0^{Tdelay} F dt,$$

where F=sample flow rate. The delay is not known, so the sampling volume can't be calculated. If two different sample flow rates are used, then:

$$Vsample = \int_0^{Tdelay1} F1 dt = \int_0^{Tdelay2} F2 dt,$$

where F1 is a sample flow rate1, Tdelay1 is a respective delay and F2 is the a sample flow rate2 and Tdelay2 is a respective delay. By changing the sample flow rate, the delay changes. If the sample flow rate is averaged during the delay time (=F1ave) in the following way:

$$F1ave = \int_0^{Tdelay1} F1 dt / \text{delay1},$$

Vsample is then:

$Vsample = F1ave * Tdelay1 = F2ave * Tdelay2$

If the difference between delays is ΔTdelay, then $Vsample = F1ave * Tdelay1 = F2ave * (Tdelay1 + \Delta Tdelay).$ Delay1 can be solved from the equation:

$Tdelay1 = F2ave * \Delta Tdelay / (F1ave - F2ave).$

The sampling volume can now be expressed with ΔTdelay and flows:

$Vsample = F1ave * Tdelay1 = F1ave * F2ave * \Delta Tdelay / (F1ave - F2ave).$

If units such as ml/min as flow unit, s as Tdelay unit and ml as volume unit are used, then $Vsample = (F1ave/60) * Tdelay1 = F1ave * F2ave * \Delta Tdelay / (60 * (F1ave - F2ave)).$ The delay can now be calculated:

$$T\text{delay} = 60 * V\text{sample}/F\text{ave},$$

where Fave is the average sample flow.

Various other features, objects, and advantages of the invention will be made apparent to those skilled in art from the accompanying drawings and detailed description thereof.

SUMMARY OF THE INVENTION

The above-mentioned shortcomings, disadvantages and problems are addressed herein which will be understood by reading and understanding the following specification.

In an embodiment, a method for determining a sample flow volume includes withdrawing a sample flow at a first and second flow rate from a gas flow, measuring a concentration of at least one gas component of the sample flow and measuring at least one of an airway pressure and flow. The method for determining a sample flow volume also includes generating first measurement results based on the measured concentration, generating second measurement results based on the measured at least one of the airway pressure and flow and setting a suitable point of comparison both among the first and second measurement results. The method for determining a sample flow volume further includes determining a first time delay between the point of comparison of the first and second measurement results of the first flow rate, determining a second time delay between the point of comparison of the first and second measurement results of the second flow rate and providing information about the first and second flow rate; and determining the sample volume based on differences between the first and second time delay.

In another embodiment, an arrangement for determining a sample flow volume includes a pump for withdrawing at first and second flow rates along a sampling tube a sample flow from a channel for a gas flow, an analyzer for measuring a concentration of at least one gas component withdrawn at the first and second flow rates and a measuring apparatus for measuring at least one of an airway pressure and flow of the gas flow when withdrawing at the first and second flow rate. The arrangement for determining a sample flow volume includes an electronics for generating first measurement results based on the measured concentration of at least one gas component withdrawn at a first and second flow rate and for generating second measurement results based on the at least one of the airway pressure and flow measured while withdrawing at the first and second flow rate. The electronics is also for setting a suitable point of comparison both among the first measurement results and among the second measurement results and for determining a first time delay between the point of comparison of the first measurement results and the point of comparison of the second measurement results of the first flow rate and for determining a second time delay between the point of comparison among the first measurement results and the point of comparison among the second measurement results of the second flow rate. Further the electronics is for receiving an information about the first and second flow rate and for determining the sample volume based on differences between the first time delay at the first flow rate and the second time delay at the second flow rate.

In yet another embodiment a method for determining a sample flow volume includes withdrawing a sample flow at a first and second flow rate from a gas flow, measuring a concentration of at least one gas component of the sample flow when withdrawing at the first and second flow rate and measuring at least one of an airway pressure and flow of the gas flow when withdrawing at the first and second flow rate. The method for determining a sample flow volume also includes generating first measurement results as a function of time based on the measured concentration of the first and second flow rate, generating second measurement results as a function of time based on the measured at least one of the airway pressure and flow of the first and second flow rate and setting a suitable point of comparison both among the first measurement results and the second measurement results of the first and second flow rate. The method for determining a sample flow volume further includes determining a first time delay between the point of comparison of the first measurement results and the point of comparison of the second measurement results of the first flow rate and determining a second time delay between the point of comparison of the first measurement results and the point of comparison of the second measurement results of the second flow rate. The method for determining a sample flow volume also includes providing information about the first flow rate and the second flow rate and determining the sample volume based on differences between the first time delay at the first flow rate and the second time delay at the second flow rate.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
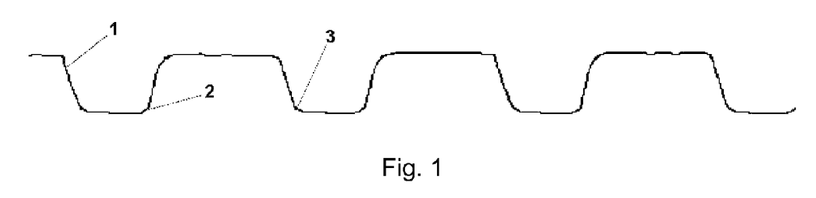
FIG. 1 illustrates a typical example of gas concentration measurement results of a breathing air.

First measurement results 1 such as gas concentration measurement results measured from a subject is shown in FIG. 1 as a curve revealing expiration and inspiration periods. This measurement result represents carbon dioxide ($CO_2$) concentration measurement as a function of time. A beginning of an expiration period is shown with a first mark 2 and a beginning of an inspiration period is shown with a second mark 3. When the subject is exhaling the carbon dioxide concentration is proving increased values and when the subject is inhaling the carbon dioxide concentration values are naturally decreasing.

Figure 2:
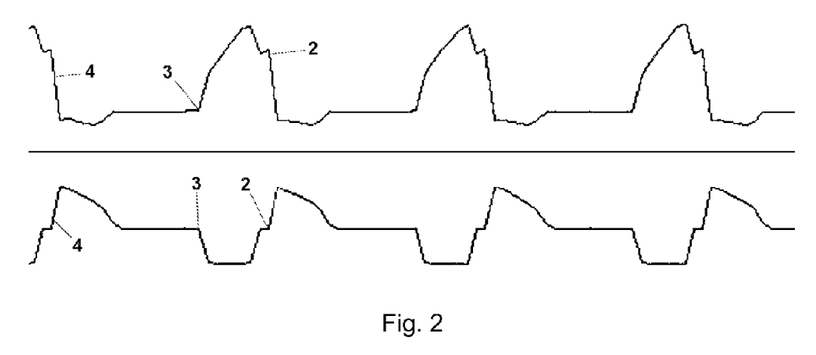
FIG. 2 illustrates a typical example of airway pressure and flow measurement results of a breathing air.

Second measurement results 4 such as spirometry measurement results are usually understood to include both an airway pressure measurement and a flow measurement. Second measurement results 4 representing both the pressure measurement results shown as a curve in an upper part of FIG. 2 and flow measurement results shown as a curve in lower part of FIG. 2 are made simultaneously. The pressure measurement is based on a pressure difference between a measurement point, which is typically in a respiratory circuit, and an environmental pressure. The flow measurement is based on a pressure difference over a restrictor in a measurement point, which is also typically in the respiratory circuit allowing an inspiration and expiration gas flow between the subject and an apparatus maintaining the respiration. The first mark 2 shows the beginning of the expiration and the second mark 3 shows the beginning of the inspiration. According to the second measurement results 4 the airway pressure when inhaling is first strongly increasing and then towards the end of the inhalation period strongly decreasing, but when exhaling the pressure is not significantly changing. Instead the flow measurement results shows a significant fall when the subject is starting to inhale as shown by the second mark 3. During the inhalation period the flow is constant and decreases to zero at the end of inhalation period (zero flow level is in the middle of the lower figure). In the beginning of exhalation period the flow increases first strongly and decreases then to zero level.

Figure 3:
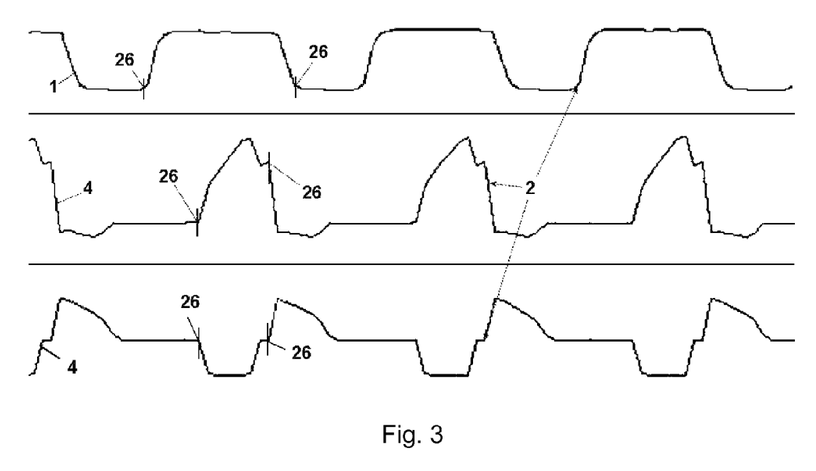
FIG. 3 illustrates an unsynchronized gas concentration measurement results in relation with airway pressure and flow measurement results.

FIG. 3 shows both the first measurement results 1 representing the gas concentration measurement of carbon dioxide and the second measurement results 4 representing the airway pressure and the flow as a function of time. The first measurement results 1 of FIG. 3 is unsynchronized in relation with the second measurement results 4. The second measurement results 4 in the lower part of FIG. 3 represent the flow measurement and those in the middle represent the airway pressure. All these measurements have been done substantially simultaneously but due to the time needed for the gas sample to arrive an analyzer the gas concentration measurement is actually made later than the airway pressure or the flow measurement. The gas concentration is measured by the sidestream technique meaning that there is a delay compared to measurements made for the airway pressure and the flow. The first mark 2 shows the beginning of the expiration period of each measurement results 1, 4 making clear that each period of the carbon dioxide measurement or any other gas component measurement made by the sidestream technique should be correctly synchronized with the same period of at least one of the airway pressure and the flow in case the measurement results including the gas concentration is utilized for some further common analysis or determination.

Figure 4:
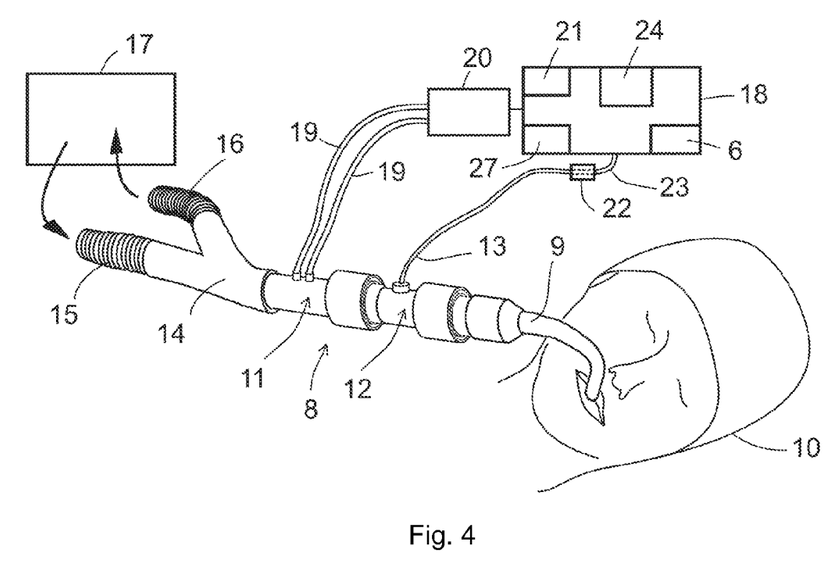
FIG. 4 is a schematic perspective view of an arrangement for a gas concentration and at least one of an airway pressure and a flow measurement in accordance with an embodiment.

A schematic view of an arrangement for the sample volume determination, when a sidestream gas concentration measurement and at least one of the airway pressure and the flow measurement is made, is shown in FIG. 4 in an operating environment where an intubation tube 9 is inserted into a windpipe of a subject 10. A gas channel 8 such as a respiratory circuit along which the gas flow is flowing is equipped with an airway adapter 12 provided with a sampling tube 13 for withdrawing a gas sample from the gas channel 8. In this specific embodiment the gas channel 8 is arranged between the intubation tube 9 and a branching unit 14, which branching unit is connectable by means of the inlet and outlet hoses 15, 16 to an apparatus 17 maintaining a respiration. Also the gas channel 8 may be equipped with a pressure adapter 11. The airway adapter 12 is normally connected so that it lies closest to the subject 10, but it could also be integrated with the pressure adapter 11 or it could be placed between the pressure adapter 11 and the branching unit 14. The gas sampling tube 13 is operably connected to an analyzer 18 for measuring the gas concentration. A pump 6 is withdrawing the sample gas to the analyzer 18. A water trap 22 removing a liquid from the sample gas together with an internal tubing 23 may be inserted between the sampling tube 13 and the analyzer 18.

The first measurement results 1 of the analyzer 18 representing gas concentration measurement are processed by electronics 21 and can be shown on a display 24 revealing e.g. the variations in the gas concentration under measurement as a function of time including the inhalation and exhalation periods. The pressure adapter 11 is also operably connected usually via at least one tube 19 to a measuring apparatus 20 to measure at least one of the airway pressure and flow. The measuring apparatus 20 is connected to the analyzer 18 or its electronics 21 for a signal processing and for producing a display of the flow and airway pressure readings for the inhalation and exhalation and possible other quantities derived from them. The electronics 21 capable of processing signals received from the measuring apparatus 20 and/or the analyzer 18 can also be elsewhere outside the analyzer 18. The measuring device 20 may also be placed in the analyzer 18. Further the analyzer 18 may be equipped with a sample flow sensor 27 as shown in FIG. 4 to measure the flow rate of the sample gas or the sample flow sensor 27 can be also inserted into the sampling tube 13.

The arrangement can also be modified for spontaneously breathing subjects, in which case no apparatus 17 maintaining the respiration is needed making also the branching unit 14 unnecessary. Also the intubation tube 9 can be replaced by a mask operably connected to the gas channel 8 having its airway adapter 12 and the pressure adapter 11.

Figure 5:
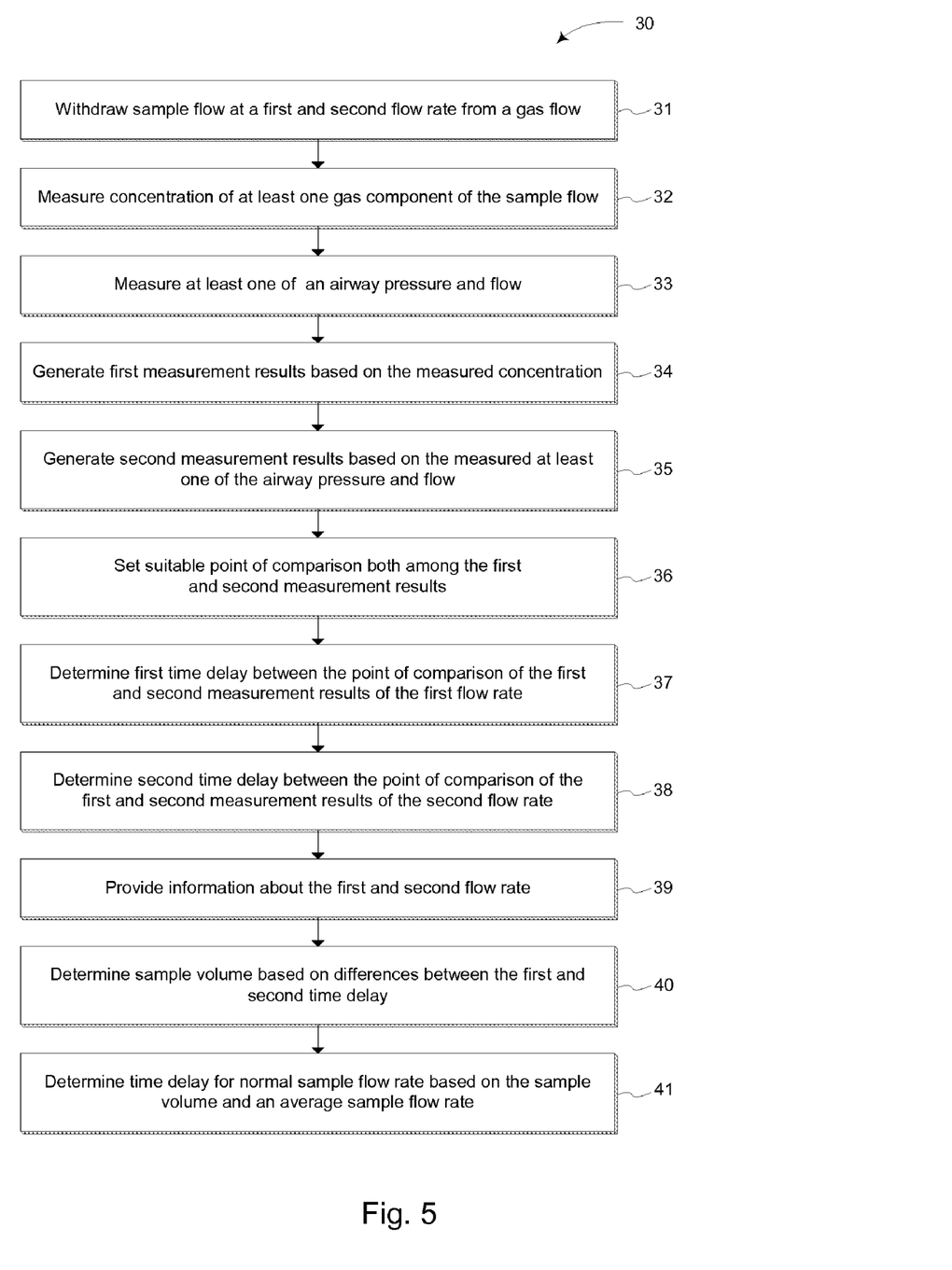
FIG. 5 is a block diagram illustrating a method in accordance with an embodiment.

FIG. 5 shows a method 30 for the sample flow volume determination. References to the arrangement of FIG. 4 have also been made while discussing the method. The sample flow volume is such volume, which is situated between the airway adapter 12 allowing the gas flow along the gas channel 8 and the analyzer 18. A part of a gas flow flowing along the gas channel 8 is withdrawn to the analyzer 18. Depending on the arrangement the main part of the sample volume may be the volume of the sampling tube 13 and the water trap 22 with the internal tubing 23, which water trap is usually involved to remove water or liquid from the sample flow. A result of the sample volume determination can be used further to calculate a delay for obtaining a gas sample from the airway adapter 12 in the gas channel 8 of the respiratory circuit between the subject 10 and the apparatus 17 maintaining the respiration, and conducting the gas sample along the sampling tube 13 to the analyzer 18 for the measurement of the gas component, which may include one of carbon dioxide and oxygen. Naturally other gas components such as anesthetic agents can also be measured. This method is also useful when the subject is spontaneously breathing in which case no apparatus 17 maintaining the respiration is needed. As explained hereinbefore the method 30 is needed while syncronising the sample gas concentration measurement with one of the airway pressure and the flow measurement. Possibly the airway pressure measurement is preferred.

At step 31 a sample flow for a gas analysis is withdrawn from the gas flow in the gas channel 8 along the sampling tube 13 at a first flow rate and a second flow rate to the analyzer 18. Withdrawing the sample flow at the first and second flow rate may be arranged in consecutive order. Usually the gas channel 8 is equipped with the airway adapter 12 in which case the sample flow is withdrawn from this airway adapter 12 and along the sampling tube 13 to the analyzer 18.

A concentration of at least one gas component of the sample flow is measured at step 32 by the analyzer 18 when withdrawing the sample flow is done at the first and second flow rate.

The concentration measurement may comprise an inhalation phase, exhalation phase and phases therebetween. Especially carbon dioxide and oxygen produce reliable measurement results to detect at least one of these phases, which can be used at later stage of the method 30. The measurement result can comprise several breathing cycles while each breathing cycle includes a period from the start of the inhalation through the expiration to the start of next inhalation.

At step 33 at least one of the airway pressure and the airway flow of the gas flow is measured by the measuring apparatus 20 connected to the gas channel 8 usually by means of the pressure adapter 11. The measurement is done when withdrawing the sample flow at the first and second flow rate. This measurement is made substantially simultaneously with the sample flow measured at step 32.

First measurement results 1 of the first and second flow rate are generated by the electronics 21 at step 34 as a function of time based on the measuring step 32 regarding the concentration measurement.

Second measurements results 4 as a function of time at step 35 are generated by the electronics 21 based on said measuring at least one of said airway pressure and flow according to step 33.

At step 36 a suitable point of comparison 26 as shown in FIG. 3 is set both among the first measurement results 1 and the second measurement results 4 of the first and second flow rate. Naturally there can be more than one point of comparison 26 chosen among the first and second measurement results. Typically the suitable point of comparison 26 is the beginning of the expiration period as shown in FIGS. 1 and 2 with the first mark 2 or the beginning of the inspiration period as shown with the second mark 3 or any other point of comparison, which can be detected or measured. With the first measurement results 1 different points of comparison 26 can be used compared to the second measurement results 4. Thus the point of comparison 26 for the first measurement results 1 can be for example the beginning of the inspiration period and the point of comparison 26 for the second measurement results 4 can be the beginning of the expiration period. The suitable point of comparison can be determined at the factory to be for example the beginning of inspiration or the beginning of expiration which can be set by the electronics but the point of comparison can be determined and set also by the electronics 21 measuring the curves shown in FIG. 3 and may select either beginning of expiration or beginning of inspiration depending on the shape of the curves of FIG. 3.

A first time delay between the point of comparison 26 of the first measurement results 1 and the point of comparison 26 of the second measurement results 4 is determined by the electronics 21 at step 37 when the withdrawing has been made at the first flow rate. Typically the point of comparison is chosen among the first measurement results after which the nearest point of comparison among the second measurement results is chosen. The delay can be determined based on single point of comparison among each of the first and second measurement results especially in mechanical ventilation when the subject is connected to the apparatus 17 maintaining the respiration and when breathing cycles can be kept constant. The determination can be also made of several successive breathing cycles and average delays between points of comparison of the first and second measurement results. This is especially advantageous if the subject is inhaling and exhaling spontaneously meaning that the breathing is irregular.

A second time delay between the point of comparison 26 of the first measurement results 1 and the point of comparison 26 of the second measurement results 4 is determined by the electronics 21 at step 38 when withdrawing the sample flow has been made at the second flow rate. Also in this case the delay can be determined based on single point of comparison among each of the first and second measurement results especially in mechanical ventilation when the subject is connected to the apparatus 17 maintaining the respiration and breathing cycles can be kept constant. The determination can be also made of several successive breathing cycles and average delays between points of comparison of the first and second measurement results.

This is especially advantageous if the subject is inhaling and exhaling spontaneously meaning that the breathing is irregular.

At step 39 an information about the first and second flow rates is provided typically to the electronics 21. The information about the first and second flow rates received by the electronics 21 may have been set already in the factory, in which case the electronics have this information, but then it may be useful to be quite sure to measure the real flow rates by means of the sample flow sensor 27 when withdrawing especially in case the flow rates may differ from the set values. The first flow rate can be for example a normal flow+10 ml/min. The second flow rate should differ from the first flow rate. It is advantageous to find such second flow rate, which differs sufficiently from the first flow rate to find time differences when various breathing phases appear in the first and second measurement results. Such sufficient differ in the first and second flow rates is at least 10 ml/min, more specifically at least 15 ml/min or even more specifically at least 20 ml/min. The second flow rate can be for example a normal flow−10 ml/min. Thus the normal sample flow rate can be different from said first and second flow rate or it can be one of the first and second flow rate. The normal sample flow rate is used in ordinary concentration measurements when the sample flow volume is already known.

At step 40 the sample volume is determined by the electronics 21 based on differences between the first time delay at the first flow rate and the second time delay at the second flow rate. The following equation can be solved:

$$V\text{sample} = F1\text{ave} * F2\text{ave} * \Delta T\text{delay} / (60 * (F1\text{ave} - F2\text{ave})),$$

where F1ave is the average first flow rate and F2ave is the average second flow rate measured by the electronics 21 of the analyzer 18. ΔTdelay is a difference between the first and second time delays. The first and second time delay are not measured but the ΔTdelay can be measured directly as a time shift change of curves between the first measurement results 1 and the second measurement results 4 at two different flow rates.

Further if needed a time delay, which is a delay between measurements 1 and 4 at normal sample flow rate, can be determined by the electronics 21 at step 41, which is optional, based on the sample volume measured hereinbefore at step 40 and the average flow rate for example solving the equation:

$$T\text{delay} = 60 * V\text{sample} / F\text{ave},$$

where Fave is the average flow rate for a normal sample flow in normal measurement mode. The average flow rate is a mean value of one or more inhalation and expiration period. The calculated Tdelay is approximately a delay between measurement results 1 and 4 and the exact delay can be determined by waiting for the Tdelay time after beginning of inspiration or expiration of measurement result 1 and selecting the nearest beginning of inspiration or expiration from measurement result 4 respectively.

In the method described hereinbefore withdrawing the sample flow at the first flow rate is followed by measuring the concentration of at least one gas component of the sample flow of the first flow rate and subsequently is made withdrawing the sample flow at the second flow rate and measuring the concentration of at least one gas component of the sample flow of the second flow rate. Also withdrawing the sample flow at the first flow rate may be made substantially simultaneously with measuring at least one of the airway pressure and flow of the gas flow. Withdrawing the sample flow at the second flow rate may be made substantially simultaneously with measuring at least one of the airway pressure and flow of the gas flow. Further withdrawing the sample flow at the first flow rate, measuring at least one of the airway pressure and flow of the gas flow when withdrawing at the first flow rate and measuring the concentration of at least one gas component of the sample flow of the first flow rate are made first followed by withdrawing the sample flow at said second flow rate, measuring at least one of the airway pressure and flow of the gas flow when withdrawing at the second flow rate and measuring the concentration of at least one gas component of the sample flow of the second flow rate.

There are several advantages of using the above described method and arrangement. The measurement of the sample volume and delay, which enables synchronization of the first measurement results 1 and the second measurement results 4, can be done at any time or even continuously or at certain intervals. The sample volume may change a bit as a function of the time because the amount of water inside sampling tube 13 varies continuously. The method can be exploited with modern existing arrangements after a modification having an arrangement equipped with the pressure or flow measuring capability and the analyzer capable of sidestream measurement. This method enables accurate gas exchange measurement with accurate measurement of the time delay.

The method can also be utilized in shortening the zeroing times of the arrangement that includes the pressure or flow measuring capability and zeroing valve, which is used to periodically draw environmental air to the analyzer. During zeroing the gas in the sampling tube is mixed mostly because of the apparatus maintaining the respiration cycles. Therefore the sampling tube has to be flushed before the first measurement results can be shown on the display. If the time for flushing is known the first measurement results can be shown immediately after the arrangement is flushed.

The method described hereinbefore can be exploited besides in patient monitoring but also in any other monitoring were samples of fluid are analyzed and simultaneously or substantially simultaneously some other measurement of the fluid of the same origin as the analyzed fluid is made and when time delays between these two measurements are needed to know.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining a sample flow volume comprising:
    withdrawing a sample flow at a first and second flow rate from a gas flow;
    measuring a concentration of at least one gas component of the sample flow;
    measuring at least one of an airway pressure and flow of said gas flow when withdrawing at said first and second flow rate;
    generating first measurement results based on said measuring the concentration;
    generating second measurement results based on said measuring at least one of said airway pressure and flow;
    setting a suitable point of comparison both among said first and second measurement results;
    determining a first time delay between said point of comparison of said first and second measurement results of said first flow rate;
    determining a second time delay between said point of comparison of said first and second measurement results of said second flow rate;
    providing information about said first and second flow rate; and
    determining the sample volume based on differences between the first and second time delay.

2. The method according to claim 1, wherein said measuring the concentration of at least one gas component of the sample flow and said measuring at least one of an airway pressure and flow is configured to be made when withdrawing at the first and second flow rate.

3. The method according to claim 1, wherein said generating first measurement results are configured to be made as a function of time and based on said measuring the concentration of the sample flow withdrawn at the first and second flow rate.

4. The method according to claim 1, wherein said generating second measurement results are configured to be made as a function of time and based on said measuring at least one of said airway pressure and flow when withdrawing at the first and second flow rate.

5. The method according to claim 1, wherein determining the sample volume is based on differences between the first time delay at said first flow rate and the second time delay at said second flow rate.

6. The method according to claim 1, wherein the sample flow volume is defined by the formula:

$$V\text{sample}=F1\text{ave}*F2\text{ave}*\Delta T\text{delay}/(60*(F1\text{ave}-F2\text{ave})),$$

where F1ave is an average first flow rate during the first time delay, F2ave is an average second flow rate during the second time delay and $\Delta T$delay is a difference between first and second time delays.

7. The method according to claim 1, further comprising determining a time delay for a normal flow rate based on said sample volume and an average flow rate.

8. The method according to claim 7, wherein said normal flow rate is different from said first and second flow rate.

9. The method according to claim 7, wherein said normal flow rate is one of said first and second flow rate.

10. The method according to claim 8, wherein said normal flow rate is used in concentration measurements when the sample flow volume is already known.

11. The method according to claim 7, wherein said time delay for the normal flow rate is calculated by the formula:

$$T\text{delay}=60*V\text{sample}/F\text{ave},$$

where Fave is an average flow rate for a normal sample flow.

12. The method according to claim 11, wherein said average flow rate is a mean value of one or more inhalation and expiration periods.

13. The method according to claim 11, wherein the calculated Tdelay is approximately a delay between said first measurement results and second measurement results and the exact delay can be determined by waiting for the Tdelay time after a beginning of an inspiration or an expiration of said first measurement results and selecting the nearest beginning of the inspiration or the expiration from said second measurement results respectively.

14. The method according to claim 1, wherein said withdrawing the sample flow at said first flow rate is followed by said measuring the concentration of at least one gas component of the sample flow of the first flow rate followed by said withdrawing the sample flow at said second flow rate and said measuring the concentration of at least one gas component of the sample flow of the second flow rate.

15. The method according to claim 1, wherein said withdrawing the sample flow at said first flow rate is made substantially simultaneously with said measuring at least one of the airway pressure and flow of said gas flow.

16. The method according to claim 1, wherein said withdrawing the sample flow at said first flow rate, said measuring at least one of the airway pressure and flow of said gas flow when withdrawing at said first flow rate and said measuring the concentration of at least one gas component of the sample flow of the first flow rate are made first followed by said withdrawing the sample flow at said second flow rate, said measuring at least one of the airway pressure and flow of said gas flow when withdrawing at the second flow rate and said measuring the concentration of at least one gas component of the sample flow of the second flow rate.

17. The method according to claim 1, wherein said first flow rate is configured to differ from said second flow rate at least 10 ml/min.

18. An arrangement for determining a sample flow volume comprising:
   a pump for withdrawing a sample flow from a channel for a gas flow along a sampling tube at a first and second flow rate;
   an analyzer for measuring a concentration of at least one gas component withdrawn at said first and second flow rates;
   a measuring apparatus for measuring at least one of an airway pressure and flow of said gas flow when withdrawing at said first and second flow rate; and
   an electronics for generating first measurement results based on the measured concentration of at least one gas component withdrawn at a first and second flow rate and for generating second measurement results based on said at least one of said airway pressure and flow of said gas flow measured while withdrawing at said first and second flow rate and for setting a suitable point of comparison both among said first measurement results and among said second measurement results and for determining a first time delay between said point of comparison of said first measurement results and said point of comparison of said second measurement results of said first flow rate and for determining a second time delay between said point of comparison among said first measurement results and said point of comparison among said second measurement results of said second flow rate and for receiving an information about said first and second flow rate and for determining the sample volume based on differences between the first time delay at said first flow rate and the second time delay at said second flow rate.

19. The arrangement according to claim 18, wherein said electronics is configured to determine a time delay for a normal sample flow rate based on said sample volume and an average flow rate.

20. A method for determining a sample flow volume comprising:
   withdrawing a sample flow at a first and second flow rate from a gas flow;
   measuring a concentration of at least one gas component of the sample flow when withdrawing at said first and second flow rate;
   measuring at least one of an airway pressure and flow of said gas flow when withdrawing at said first and second flow rate;
   generating first measurement results as a function of time based on said measuring the concentration of said first and second flow rate;
   generating second measurement results as a function of time based on said measuring at least one of said airway pressure and when withdrawing at the first and second flow rates;
   setting a suitable point of comparison both among said first measurement results and said second measurement results of the first and second flow rate;
   determining a first time delay between said point of comparison of said first measurement results and said point of comparison of said second measurement results of said first flow rate;
   determining a second time delay between said point of comparison of said first measurement results and said point of comparison of said second measurement results of said second flow rate;
   providing information about said first flow rate and said second flow rate; and
   determining the sample volume based on differences between the first time delay at said first flow rate and the second time delay at said second flow rate.

* * * * *

UNITED STATES PATENT AND TRADEMARK OFFICE
CERTIFICATE OF CORRECTION

PATENT NO. : 8,333,111 B2
APPLICATION NO. : 12/858857
DATED : December 18, 2012
INVENTOR(S) : Hietala Page 1 of 1

It is certified that error appears in the above-identified patent and that said Letters Patent is hereby corrected as shown below:

In Column 11, Line 7, in Claim 14, delete "rate" and insert -- rate, --, therefor.

Signed and Sealed this
Sixteenth Day of April, 2013

Teresa Stanek Rea
*Acting Director of the United States Patent and Trademark Office*